United States Patent [19]
Van Mierlo

[11] Patent Number: 4,974,606
[45] Date of Patent: Dec. 4, 1990

[54] HEARING PROTECTOR AND METHOD OF MANUFACTURING THE SAME

[75] Inventor: Cornelis M. Van Mierlo, Budel, Netherlands

[73] Assignee: Safetec S.A., Luxembourg

[21] Appl. No.: 323,619

[22] Filed: Mar. 14, 1989

[30] Foreign Application Priority Data

Mar. 17, 1988 [NL] Netherlands .................. 8800672

[51] Int. Cl.$^5$ .................................... A61F 11/00
[52] U.S. Cl. .................................. 128/864; 181/130
[58] Field of Search .......................... 181/130–135; 138/864–868

[56] References Cited

U.S. PATENT DOCUMENTS

| | | | |
|---|---|---|---|
| 2,881,759 | 4/1959 | Hocks et al. ................. | 128/868 |
| 3,565,069 | 2/1971 | Miller ........................... | 128/867 |
| 3,783,864 | 1/1974 | Moller ........................... | 128/864 |
| 4,412,096 | 10/1983 | Edgerton et al. .............. | 181/130 X |
| 4,587,965 | 5/1986 | de Boer et al. ................ | 128/867 |
| 4,729,451 | 3/1988 | Brander et al. ................ | 181/130 |

*Primary Examiner*—Robert A. Hafer
*Assistant Examiner*—Lynda M. Cofsky
*Attorney, Agent, or Firm*—Peter L. Michaelson

[57] ABSTRACT

A hearing protector has a body made of a suitable material and matching the shape of the auricle or ear shell and/or the auditory canal of the user. The body is provided with a canal which, in the condition wherein the body is placed within an ear of the wearer, provides communication between the auditory canal and a free space of the body. The body includes a second canal which, like the first canal, extends between the auditory-canal end and the free-space end of the body. An adjustable damping member is provided in or on the first canal for damping sound to suit the wearer's comfort in conditions in which the device is used.

15 Claims, 2 Drawing Sheets

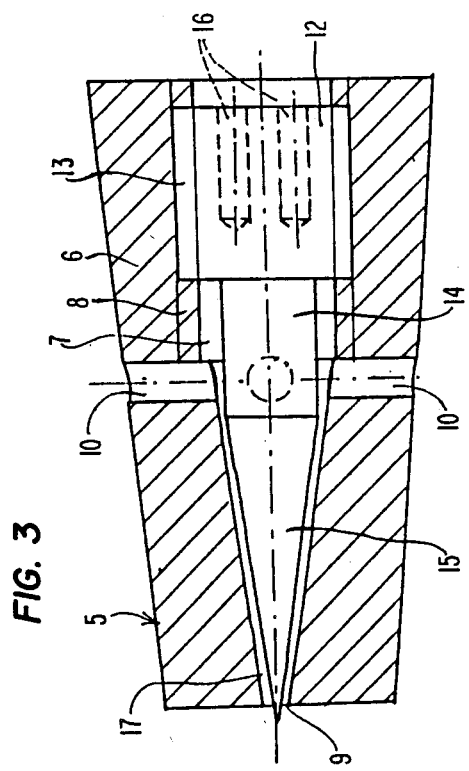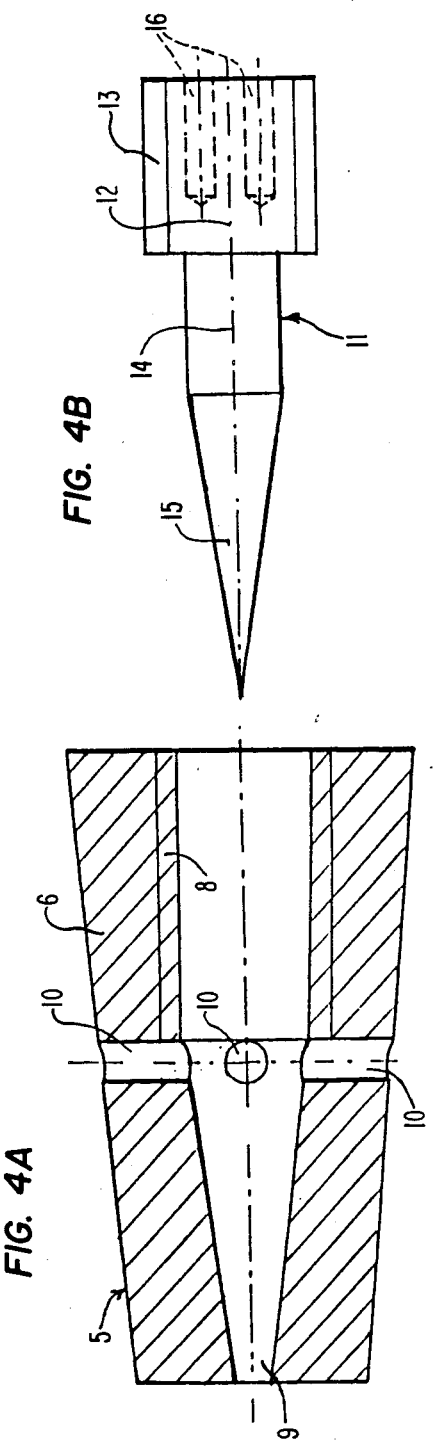

HEARING PROTECTOR AND METHOD OF MANUFACTURING THE SAME

This invention relates to a hearing protector, comprising a body of a suitable material, the shape of said body being adapted to the shape of the auricle or ear shell and/or auditory canal of the intended wearer of the device, said body being provided with a canal which, in the condition in which the body is placed within an ear of the wearer, provides a communication between the auditory canal and the free space, while moreover means are provided in or on the body for damping the sound transmitted through said canal. The present invention further relates to a method of manufacturing a hearing protector.

A hearing protector or otoplast as defined hereinbefore is known and commercially available. The known hearing protector contains an acoustic filter or otherwise formed constriction in the canal, which filter or constriction damps the sound transmitted through the canal. A concomitant problem is that once a filter or constriction has been placed it can no longer be changed, unless by replacement of the filter or constriction. The known otoplasts are supplied with a standard series of acoustic filters. Depending upon the envisaged use, a filter is determined and an otoplast comprising said filter is supplied. Consequently, hearing protectors are only available with a limited number of damping values or characteristics. Intermediate values can be supplied only upon request, for these have to be manufactured separately. Another problem is that once an otoplast is placed within the ear, its performance can only be measured by checking the leak-tightness of the arrangement; however, its other properties, such as actual damping and the like can no longer be determined.

It is an object of the present invention to provide a hearing protector lacking the above drawbacks. This object is achieved with a hearing protector whose body is provided with a second canal which, like the first canal, extends between the auditory-canal end and the free-space end of the body, while the means for damping sound comprise an adjustable damping member in or on the first canal.

By virtue of the second canal provided in the otoplast in accordance with the present invention, which canal can be used as a measuring canal, it is possible to effect measurements of the hearing protector once it has been placed inside the ear. Not only can it thus be established whether there are acoustic leaks, air leaks or otherwise between otoplast and the wall of the auditory canal, but it is also possible to measure whether the damping resistance has the desired value. By further employing an adjustable damping member, the damping resistance can be accurately set at the desired value and this setting can be accurately checked through use of the second canal.

Preferably, the adjustable damping member of the hearing protector according to the present invention is an infinitely variable reducing valve. Such an acoustic reducing valve may be integral with the hearing protector or be fitted thereon or therein as a separate part. The reducing valve is arranged so as to link up with, or extend into, the first canal and, by means of said valve, the inlet opening can be reduced infinitely until complete closure is achieved. In the latter case, with a device positioned inside the ear of the user, the auditory canal of the user is likewise entirely insulated from the surroundings, owing to the mass of the otoplast placed inside the ear, except that a connection is provided to the surrounding space through the second canal. This connection is broken by connecting a measuring apparatus to the second canal. A superatmospheric pressure can be created in the auditory canal through the measuring apparatus and the second canal, and when the reducing valve is actually fully closed, such superatmospheric pressure can only be maintained if there are no openings between the wall of the otoplast and the wall of the auditory canal. In this way the proper fit of the otoplast in the ear can be checked.

After it has been established that a hearing protector according to the present invention properly fits in the ear of the user, and that no air leaks occur, adjustment of the reducing valve can take place, so as to set the desired damping value. This is again measured through the second canal, which is connected to the gauge for the purpose. When all measurements have been effected the second canal can be sealed off in a suitable manner. For the daily use of the hearing protector according to the present invention, the second canal is no longer required. Yet the presence of the second canal is useful, since in cases where there is a change in the conditions of use, the second canal can be reopened and the reducing valve can be readjusted in the above-described manner to adapt the damping resistance to such changed operating conditions. Naturally, the second canal can always be used for inspection purposes if conditions have not changed. The second canal may be a closed canal in that a membrane is incorporated therein. It will be clear that in that case, the above-described measurements should be effected in a slightly different manner.

It will be understood that where the adjustable damping member of the hearing protector according to the present invention is an integral part of the protector or where it is a part that is separately fitted into the protector, the damping resistance of the member can be preset in the production laboratory to an approximate value. As such, once the hearing protector is installed in a user's ear, then thereafter only a minor correction will need to be made in the damping value, while the performance of the protector is being adjusted.

In a preferred embodiment of the hearing protector according to the present invention, the infinitely variable reducing valve comprises a needle housing with a needle chamber which tapers from a cylindrical bore in the housing to an outlet opening communicating with the first canal, as well as an adjusting needle, having a cylindrical portion and a conical end extending from the cylindrical portion. Suitably, at the base of the needle chamber, a plurality of radially extending canals provide a communication between the needle chamber and the exterior of the reducing valve extending into the free space. Furthermore, the cylindrical bore may be internally threaded and the adjusting needle attached to a threaded cylindrical foot having means for engagement by a screw driver, wrench or like tool. Preferably, the needle housing is frusto-conical and has the end of the truncated cone having the smaller diameter received in a fitting bore linking up with the first canal in the body of the hearing protector and is fixed in said bore, so that the portion of the needle housing projecting from the body can function as a hand grip. In operating condition, the second canal in the otoplast according to the present invention is hermetically sealed, preferably by a plug inserted into the canal from the free space. Preferably, the plug of a protector destined for the left ear is visible distinct from the plug of a device destined for the right ear, so that the plug serves as a left/right code.

In the above preferred embodiment of the hearing protector according to the present invention, the adjusting needle, which is screwed into the needle housing and has a conical shape to match said housing, fits in said housing in hermetically sealed relationship, when the adjusting needle is entirely screwed home. By screwing the adjusting needle back from this home position, a space is formed between the needle and the conical inner wall of the needle housing. This space provides a communication between the radial canals and the outlet opening, thereby connecting the auditory canal of the user with the free space outside the otoplast. Inasmuch as the size of the passage thus formed decisive the damping resistance or characteristic of the protector, the variability of this size permits the damping assistance to be adjustable.

Suitable material for the hearing protector according to the present invention are those used for known otoplasts, e.g. synthetic plastics material of the acrylate type. The acoustic reducing valve may consist of synthetic plastics material. The adjusting needle may consist of synthetic plastics material or a material having metallurgical properties.

The method according to the present invention for manufacturing the hearing protector according to the present invention is characterized to in that, on the basis of an impression of the auricle or ear shell and/or auditory canal of the intended wearer, a body is made whose shape conforms to the shape of the auricle or ear shell and/or auditory canal of the intended wearer. Two acoustically parallel canals are bored in the body, to provide communication between the auditory canal end of the body and the free space. A reducing valve is fitted on the free-space end in a bore linking up with the first canal. The body is then placed in the ear of the intended wearer. Testing and measuring devices are connected to the second canal to check whether the hearing protector can be placed with sufficient leak-tightness. If necessary, the shape of the body further adapted so as to obtain the desired leak-tightness. In addition the reducing valve is subsequently set such that the protector provides the correct damping value. Thereafter, the body of the protector is removed from the ear, and the second canal is hermetically sealed off. The setting of the reducing valve is locked, if desired.

In the above described manner, an otoplast is made which entirely conforms to the shape of the auditory canal of the intended user. The result is a personal hearing protector, the damping of which can be fully adjusted to the working situation of the wearer.

One embodiment of the hearing protector according to the present invention will now be described, by way of example, with reference to the accompanying drawings, in which:

FIG. 3 is a cross-sectional view of the reducing valve of the device shown in FIG. 1; and FIGS. 4A and 4B collectively depict similar illustration of the reducing valve shown in FIG. 3 but in an "exploded" view.

In the figures, like parts are indicated by like reference numerals.

Figure 1:
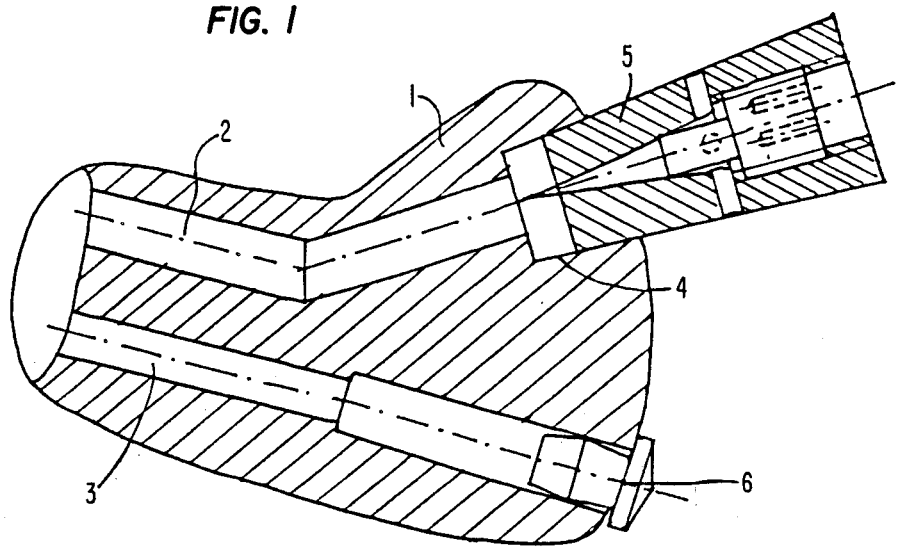
FIG. 1 is a cross-sectional view of an embodiment of the hearing protector, according to the present invention, in a ready for use condition.
Figure 2:
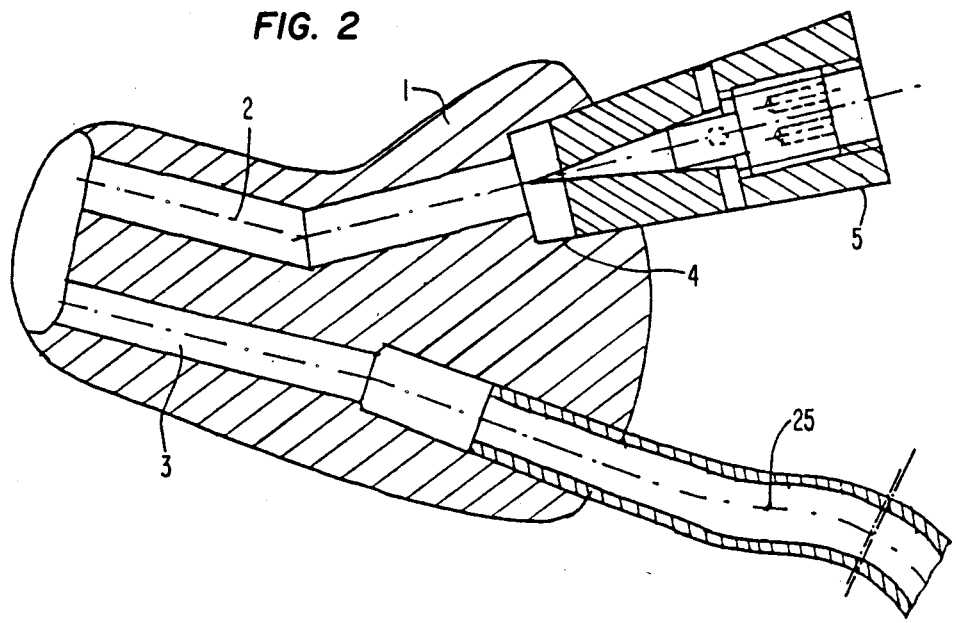
FIG. 2 is a similar view of the hearing protector of FIG. 1 during the testing of the leak-tightness and the setting of the reducing valve.

The embodiment of the hearing protector according to the present invention shown in FIGS. 1 and 2 comprises a body 1 made of a suitable synthetic plastics material, e.g. acrylate. The shape of the body 1 entirely conforms to the shape of the auditory canal of the intended user of the hearing protector. The body 1 is made e.g. by first preparing an impression in wax or like material of the auditory canal of the user and subsequently making from that impression a cast in acrylate. The cast can be finished by hand to the extent it does not conform fully to the auditory canal of the user. Two canals 2, 3 are provided in the body 1, both forming a communication between, on the one end, the auditory canal end of body 1 (left in FIGS. 1 and 2) and on the other, the free-space end of body 1 (right in the figures).

The first canal 2 is enlarged at the free-space end, by a bore 4 drilled from that end. The reducing valve 5 is secured in bore 4. Said valve 5, which will be described in more detail with reference to FIGS. 3, 4A and 4B is secured in bore 4, e.g. by gluing. Other methods of fixing are of course possible. If desired, the reducing valve 5 may be integral with the body 1. The portion of reducing valve 5 that projects from bore 4 forms a hand grip by means of which the user can position the hearing protector in his ear and remove it.

The second canal 3 in the body 1 of the hearing protector according to the present invention is a canal that functions during testing and adjustment of the hearing protector. During daily use of the otoplast, the second canal 3 is not used and, as shown in FIG. 1, is hermetically sealed off by a plug 6 introduced into canal 3 from the free-space end. The plug is made of a suitable material, e.g. a suitable synthetic plastics material. By imparting to the plug 6, for an otoplast according to the present invention destined for the left ear of the user, a colour differing from that of the plug destined for the otoplast for the right ear, the plug can likewise function as a left/right code.

In testing and adjusting the hearing protector according to the present invention, a hose 25 of a measuring and regulating appliance (not shown) is connected to the second canal 3, as illustrated in FIG. 2. Hose 25 extends, e.g, from the free-space end into an enlarged portion of canal 3. By means of this appliance, when reducing valve 5 is closed a super-atmospheric pressure can be generated at the auditory-canal end of body 1 through hose 25 and canal 3, which permits determining whether the otoplast fits the auditory canal of the user in a leak-tight manner. If necessary, body 1 can be trimmed to obtain an entirely leak-tight fit. Subsequently, the reducing valve is adjusted and set at the desired damping valve.

FIGS. 3, 4A and 4B show the reducing valve 5 in further detail. Valve 5 comprises a somewhat conically tapered body or needle housing 6, made e.g. of synthetic plastics material and having a central bore 7. In the widest portion of the conical needle housing 6, the bore is cylindrical and has internal threading 8. In the tapered portion of needle housing 6, bore 7 is likewise tapered or conical, terminating in the opening 9 in the front wall of housing 6. At the location where the cylindrical portion of bore 7 merges into the conical portion, four radial canals 10, uniformly interspaced, communicate with the free space.

Needle housing 6 accommodates the adjusting needle 11, shown in FIG. 4B removed from housing 6. Needle 11, which is made e.g. of synthetic plastics material or a material having metallurgical properties, comprises a first cylindrical portion 12 whose dimensions correspond with those of the cylindrical portion of bore 7 in needle housing 6. Cylindrical portion 12 is threaded at 13 so that needle 11 can be screwed into housing 6. Needle 11 has a reduced cylindrical portion 14 adjacent to cylindrical portion 12, and which, in turn, merges into a tapered end portion 15. Cylindrical portion 12 of needle 11 contains two parallel bores 16 extending parallel to, and symmetric with respect to the axis of needle 11. Bores 16 serve as points of engagement for a special type of wrench or screw driver used for setting the reducing valve. This type of screw driver is not provided at its end with a blade but with two parallel needles fitting into bores 16.

FIG. 3 shows how needle 11 fits in needle housing 5. As illustrated in FIG. 3, needle 11 has not yet been screwed home. When needle 11 has been screwed home in housing 6, the wall of the conical portion 15 of needle 11 touches the inner wall of the conical portion of bore 7, so that the valve is hermetically sealed. When the needle is slightly screwed back, there is produced a slit 17 between the needle tip 15 and the wall of the bore 7. Slit 17 constitutes a connection between the radical canals 10 and opening 9. By screwing out needle 11 to a greater or lesser extent, the dimensions of slit 17 can be infinitely adjusted.

In an embodiment of the hearing protector according to the present invention that has been reduced to practice, the needle housing 5 had a length of 11.0 mm. It was conically formed with a minimum diameter of 4.0 mm and a maximum diameter of 6.0 mm. Needle housing 5 contained a bore having at its larger end a cylindrical portion with a diameter of 3.0 mm and a length of 5.0 mm and provided having screw thread M3 with a pitch of 0.25 mm. The connecting portion of the bore tapered conically over a length of 6.0 mm with a maximum diameter at the end of the cylindrical portion being 2.0 mm and a minimum diameter at the opening 9 of 0.6 mm. At the transition being the cylindrical portion to the conical portion of the bore, four radial canals 10, uniformly interspaced were provided with, each canal 10 having a diameter of 0.7, mm. The needle 11 fitting which fits into needle housing 5 had a first cylindrical, threaded portion with a pitch of 0.25 mm and a length of 3.0 mm. This portion 12 had such a diameter that it properly fits into in the cylindrical portion of bore 7. A second cylindrical portion 14, 14 was connected to the first portion 12 of the needle 11. This second portion has a diameter of 1.6 mm and a length of 2.5 mm. Next, needle 11 comprised a conically tapered portion 15 with a length of 5.0 mm. Cylindrical portion 12 contained two bores 16 situated parallel to one another and to the axis of needle 11 with a diameter of 5.0 mm, a depth of 2.0 mm and a pitch measure of 1.0 mm. These bores fitted a wrench that has two cylindrical pins at its end and was used for adjusting the position of the needle in the needle housing. By means of adjusting needle 11, the passage to the auditory-canal side of the reducing valve could be reduced infinitely from a surface are of about 0.283 mm$^2$ to a surface area of 0 mm$^2$ (entirely closed).

One advantage of the hearing protector according to the present invention and the method for its manufacture according to the present invention is that the resulting hearing protection is entirely tuned to the user, and its adjustment and setting can take place in vivo.

I claim:

1. A hearing protector comprising:
a body having a shape that conforms to a shape of an auditory canal of a wearer, wherein the body has a first canal therethrough for establishing communication between the auditory canal and free space outside the auditory canal and comprises means for damping sound transmitted through said first canal; characterized in that:
said body comprises a second canal therethrough, which establishes communication between said auditory canal and said free space, for use in measuring a value of a pre-defined characteristic associated with the performance of said protector while the protector is being worn by the wearer, said second canal being sealed during normal use of the protector; and
said damping means comprises an adjustable damping member connected to a first end of said first canal that is exposed to the free-space.

2. A hearing protector as claimed in claim 1, characterized in that the adjustable damping member is an infinitely variable reducing valve.

3. A hearing protector as claimed in claim 2, characterized in that the second canal is hermetically sealed by a plug inserted into an end of the second canal that is exposed to said free space.

4. A hearing protector as claimed in claim 2, characterized in that the infinitely variable reducing valve comprises a needle housing having a needle chamber that tapers conically from a cylindrical bore in the needle housing to an outlet opening linking up with the first end of the first canal and an adjusting needle for insertion within said needle housing and having a cylindrical portion and a conical end extending from the cylindrical portion.

5. A hearing protector as claimed in claim 4, characterized in that the cylindrical bore is internally threaded and that the adjusting needle is attached to a threaded cylindrical foot having means for engagement by a tool.

6. A hearing protector as claimed in claim 4, characterized in that the second canal is hermetically sealed by a plug inserted into an end of the second canal that is exposed to said free space.

7. A hearing protector as claimed in claim 4, characterized in that said chamber further comprises a plurality of radially extending canals situated at a base of the needle chamber for providing communication between the needle chamber and the free space located exterior to the reducing valve.

8. A hearing protector as claimed in claim 7, characterized in that the cylindrical bore is internally threaded and that the adjusting needle is attached to a threaded cylindrical foot having means for engagement by a tool.

9. A hearing protector as claimed in claim 7, characterized in that the second canal is hermetically sealed by a plug inserted into an end of the second canal that is exposed to said free space.

10. A hearing protector as claimed in claim 7, characterized in that the needle housing has a frusto-conical shape with opposing end surfaces of minimum and maximum diameter wherein the end surface of the needle housing having the minimum diameter extends into and is secured within a bore in the body and connected to the first end of the first canal, whereby a portion of the needle housing projecting from said body can function as a hand grip.

11. A hearing protector as claimed in claim 4 characterized in that the needle housing has a frusto-conical shape with opposing end surfaces of minimum and maximum diameter wherein the end surface of the needle housing having the minimum diameter extends into and is secured within a bore in the body and connected to the first end of the first canal, whereby a portion of the needle housing projecting from said body can function as a hand grip.

12. A hearing protector as claimed in claim 1, characterized in that the second canal is hermetically sealed by a plug inserted into an end of the second canal that is exposed to said free space.

13. A hearing protector as claimed in claim 12 characterized in that the plug of the protector destined for the left ear is visibly distinct from the plug of the protector destined for the right ear, whereby the plug serves as a left/right code.

14. A method of manufacturing a hearing protector for a wearer comprising the steps of:

forming a body that conforms to the shape of an auditory canal of the wearer;

boring first and second acoustically parallel canals through said body to provide communication between an auditory canal end of said body and a free space end of the body;

fitting a reducing valve into a first end of said first canal that is exposed to said free space;

placing the body within an ear of the wearer such that the auditory canal end of the body extends into the auditory canal of the wearer;

connecting testing and measuring means to a first end of said second canal that is exposed to said free-space, determining, in response to measurements provided by said testing and measuring means, whether a sufficient leak-tight condition exists between the auditory canal of the wearer and the body, and, if such a condition does not exist, trimming the shape of the body as needed to provide such a connection;

adjusting the reducing valve to a setting that provides a correct damping value;

removing the body from the ear of the wearer; and hermetically sealing the first end of said second canal after the body has been removed from the ear.

15. The method in claim 14 further comprising the step of locking the setting of the reducing valve after said body has been removed from the ear.

* * * * *